(12) United States Patent  
Mosley et al.

(10) Patent No.: US 8,575,539 B2  
(45) Date of Patent: Nov. 5, 2013

(54) DETECTION APPARATUS AND METHOD (75) Inventors: Alan Mosley, Hertfordshire (GB); Gihan Ryu, Surrey (GB); Hongjin Jiang, Sunnyvale, CA (US)

(73) Assignee: Molecular Vision Limited, London (GB)

( * ) Notice: Subject to any disclaimer, the term of this patent is extended or adjusted under 35 U.S.C. 154(b) by 447 days.

(21) Appl. No.: 12/669,420

(22) PCT Filed: Jul. 23, 2008

(86) PCT No.: PCT/GB2008/002527
§ 371 (c)(1),
(2), (4) Date: Jun. 23, 2010

(87) PCT Pub. No.: WO2009/013494
PCT Pub. Date: Jan. 29, 2009

(65) Prior Publication Data
US 2010/0264337 A1 Oct. 21, 2010

(30) Foreign Application Priority Data

Jul. 23, 2007 (GB) .................................. 0714341.5

(51) Int. Cl.
*G02F 1/01* (2006.01)
(52) U.S. Cl.
USPC ......... 250/225; 250/458.1; 356/364; 356/491

(58) Field of Classification Search
USPC ................... 250/221, 225, 550, 458.1, 459.1; 356/364, 491, 601, 625
See application file for complete search history.

(56) References Cited

U.S. PATENT DOCUMENTS

| 5,943,129 A | 8/1999 | Hoyt et al. |
| 6,016,177 A | 1/2000 | Motomura et al. |
| 2002/0101566 A1* | 8/2002 | Elsner et al. .................. 351/200 |

FOREIGN PATENT DOCUMENTS

| DE | 4300723 A1 | 7/1994 |
| WO | 0242747 A1 | 5/2002 |
| WO | 2007054710 A2 | 5/2007 |

* cited by examiner

*Primary Examiner* — Kevin Pyo
(74) *Attorney, Agent, or Firm* — Hickman Palermo Truong Becker Bingham Wong LLP (57) ABSTRACT

A detector apparatus and method for detecting radiation emitted from a target comprising: a first transmissive polarizer (302) for polarizing radiation incident on the target; a second transmissive polarizer (304) for polarizing the radiation emitted from the target (303) and absorbing any remaining light polarized by the first polarizer; and at least one reflective polarizer (306) arranged between the first and second transmissive polarizers.

28 Claims, 7 Drawing Sheets

Prior Art

DETECTION APPARATUS AND METHOD

This application is the National Stage of International Application No. PCT/GB2008/02527, filed on Jul. 23, 2008, which claims priority to and benefit of United Kingdom Patent Application No. 07143414.5, filed on Jul. 23, 2007.

The present invention relates to a detection apparatus and method.

There is a well established and growing need for the detection of biological compounds, e.g. albumin, troponin I, which are markers for medical conditions in samples taken from either humans or animals. At the present time the vast majority of tests carried out to detect biological compounds in a sample are carried out using laboratory based equipment. Such tests require transport of the sample to be tested to the laboratory from the place where the sample was taken from the patient or animal. This can cause delays in obtaining the results of the analysis, which may be clinically disadvantageous. Laboratory based detection systems often use fluorescent dye molecules to determine the concentration of the analyte. This is generally achieved by using a laser light source, detection optics at 90° to the source (such that light directly from the source is not detected), and a highly sensitive light detector, such as a photomultiplier tube (PMT).

More recently, diagnostic systems have been developed and commercialized that can be used at the point of care, thereby obviating the need for transportation of the sample and the consequential delay. Such diagnostic systems normally contain a cartridge into which a small sample of a bodily fluid from the patient, or animal, is applied. The cartridge also contains reagents that will selectively bind to or react with the biological marker of interest. In order to determine the concentration of the biological marker, the cartridge is then inserted into a "reader" which uses one of a wide range of techniques to determine the concentration of the biological marker. In very many cases these cartridge-reader systems require novel assays because they are not suitable for use with the fluorescence-based assays being used in the laboratory-based systems. This is because the use of a laser light source, 90° detection optics and a PMT lead to bulky and expensive optics.

Figure 1:
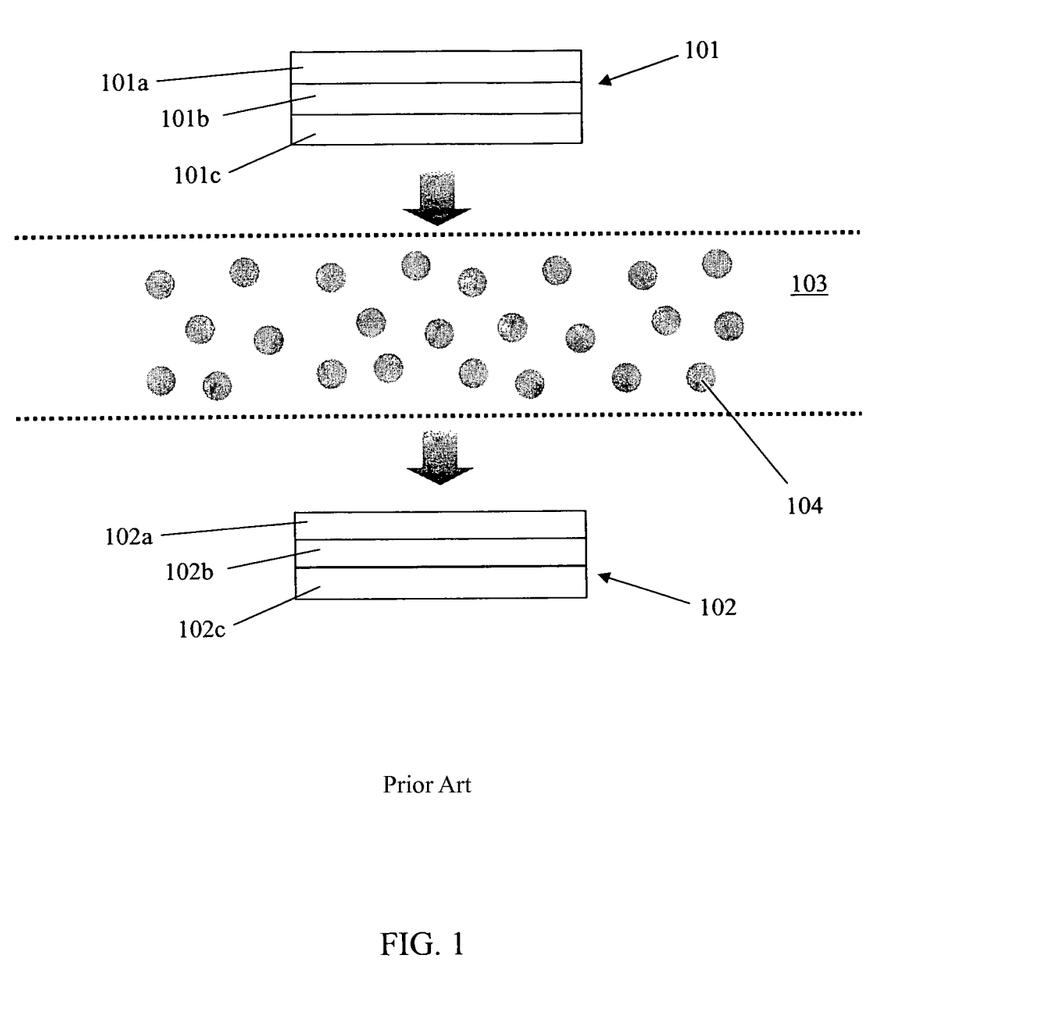
FIG. 1 shows a known optical detection system using a semi-conducting polymer detector and light source.

An example of an optical detection system which makes use of light detectors based on semiconducting polymers is described in WO02/42747. A system of this kind is illustrated in FIG. 1. This system comprises a light source 101 and a light detector 102. The source comprises a transparent electrode 101c, for example Indium Tin Oxide, and a metallic electrode, 101a, for example calcium covered with aluminium on either side of an active layer, 101b. The detector comprises a transparent electrode 102a, for example Indium Tin Oxide, and a metallic electrode, 102c, for example aluminium, on either side of an active layer, 102b. The light source 101 and light detector 102 are positioned in an opposed relationship with a chamber 103 for containing a sample positioned therebetween. Fluorescent particles 104 absorb a portion of the light from the light source 101 and emit fluorescent light which is detected by the detector 102.

Figure 2:
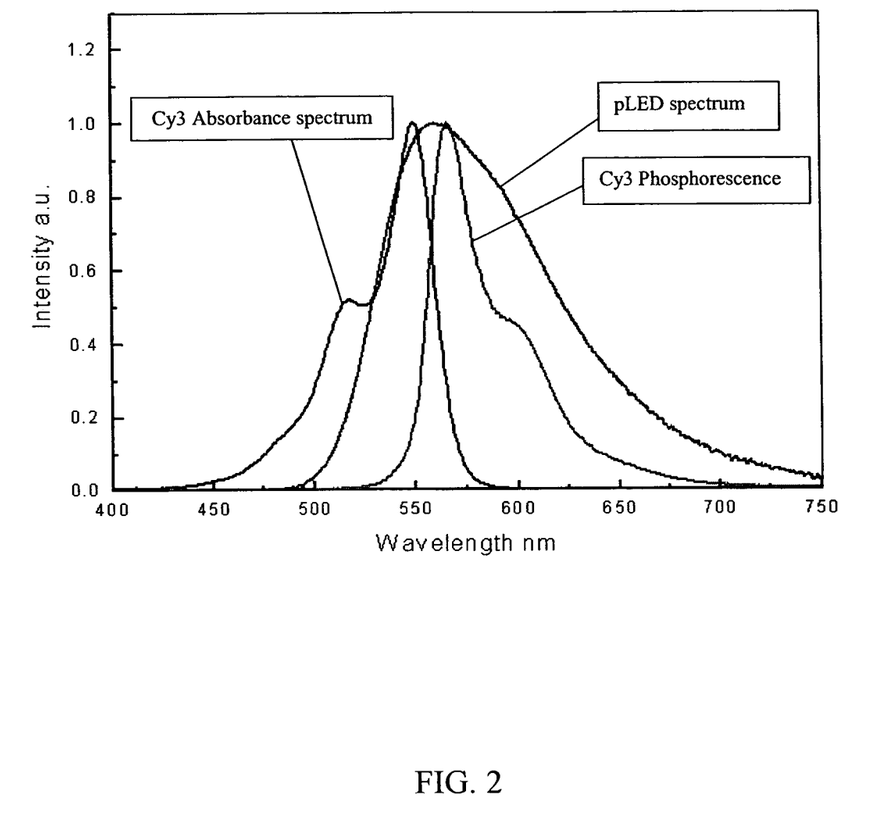
FIG. 2 shows an example of the Stokes shift produced by the fluorescent dye marker Cy3.

In a typical system of this kind illustrated in FIG. 1 the light source 101 has a spectral width of 100 nm (full-width half-maximum) and would therefore overlap the light emitted from a typical fluorescent dye marker, which generally has a Stokes shift of 30-50 nm. This overlap is illustrated in FIG. 2 which shows the spectra of the light source (yellow pLED in the embodiment shown) which has a peak at approximately 560 nm and the fluorescent dye Cy3 which has an absorbance peak at approximately 550 nm and a fluorescence or emission peak at approximately 570 nm. FIG. 2 shows that the spectrum of the light source significantly overlaps that of the fluorescence. This makes it difficult to isolate the fluorescent light from that of the light source.

In view of this spectral overlap, in order for a system of the kind shown in FIG. 1 to provide accurate data at meaningful concentrations of the analyte when detecting fluorescent or phosphorescent markers, it necessary for virtually all of the light from the light source 101 to be eliminated after it has passed through the sample so that it does not reach the light detector 102 and cause anomalous results.

WO02/42747 describes the inclusion of light-emitting diodes in microcavities to provide excitation sources having improved spectral properties, the use of notch filters in front of photocells to filter out photons transmitted directly from light-emitting diodes and phase-sensitive lock-in techniques. This makes it possible to discriminate between excitation photons transmitted from the light-emitting diode and the less-intense emission photons from the target at the expense of significantly increasing the cost of the detection system.

The invention is as set out in the claims. The present invention provides a low cost optical detection system that can be used in an in-line (0°) detection geometry with a fluorescent dye that has a Stokes shift, such as 30-50 nm, and/or a light source whose spectrum overlaps significantly both the absorption and emission spectra of the fluorescent dye to be detected. In addition, the present invention provides an optical detection system that enhances the intensity of fluorescent or phosphorescent light emitted from a sample. Hence, there is provided an improved optical detection system for detection of biological markers in a sample by fluorescence or phosphorescence techniques that are accurate and sensitive and sufficiently compact to enable use at the point of care. Furthermore, the system is low cost to provide a disposable product. In particular, embodiments aim to use a compact light detector such as semi-conducting polymer photodetector and compact light sources such as an organic light emitting diodes.

The detection system is compact because 0° detection optics are used. The size is further reduced by using thin film light sources and light detectors based on semiconducting polymers or small molecules.

Embodiments of the invention will now be described by way of example with reference to the drawings in which.

In overview, there is provided a detection apparatus for detecting radiation emitted from a target. A first transmissive polariser arranged to polarise radiation incident on the target and a second linear polariser, having a polarisation direction orthogonal to the first, arranged for polarising the emitted radiation and absorbing any remaining light polarised by the first polariser. At least one reflective polariser arranged between the first and second transmissive polarisers increases the amount of emitted radiation detected by a detector arranged to receive light transmitted by the second transmissive polariser.

Figure 3A:
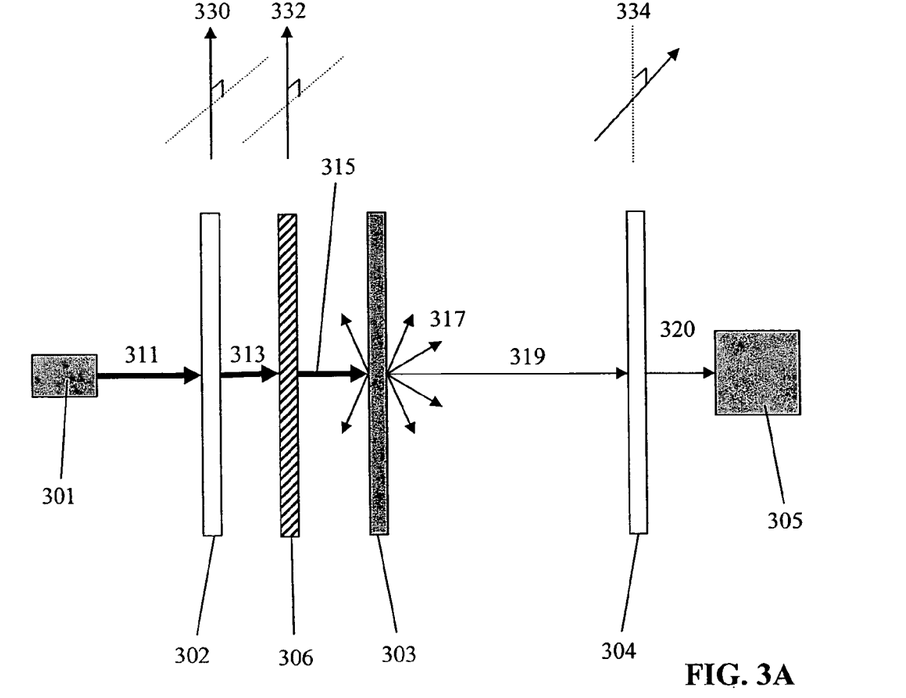
FIGS. 3A and 3B are schematics of the a first embodiment of the present invention.
Figure 3B:
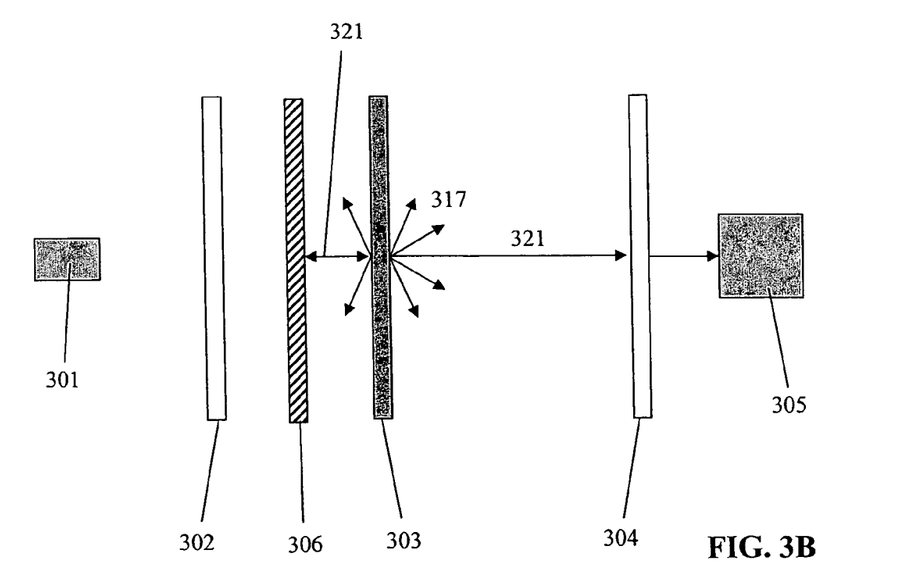

Referring to FIGS. 3A and 3B there is shown a first embodiment of the present invention comprising in series: a light source 301; a first transmissive linear polariser 302; a reflective linear polariser 306; a sample or sample chamber 303; a second transmissive linear polariser 304; and a light detector 305.

A reflective polariser is a polariser which transmits radiation in one polarisation direction and reflects radiation polarised in the orthogonal direction. A transmissive polariser is a polariser which transmits radiation in one polarisation direction and absorbs radiation polarised in the orthogonal direction.

The polarisation directions of the first transmissive linear polariser 302 and the second transmissive linear polariser 304 are orthogonal. The properties of the reflective linear polariser 306 are that it transmits light polarised in the same orientation as the linear polariser 302, but reflects light polarised orthogonally.

Referring to FIG. 3A, therefore, light 311 from light source 301 passes through first transmissive linear polariser 302 to produce linearly polarised light 313 having a polarisation direction parallel to that of the first transmissive linear polariser 302 as shown by diagram 330. Polarised light 313 then passes through reflective linear polariser 306 since the polarisation axis of polarised light 313 is parallel to that of polariser 306 as shown by diagram 332. Linearly polarised light 315 is then incident upon sample 303. If sample 303 contains a fluorophor, it will absorb light 315 and emit unpolarised fluorescent light 317. A large portion of this forward-emitted fluorescent light 319, will travel towards the photodetector, 305, and the portion of this light, 320, having a polarisation direction parallel to that of the second transmissive linear polariser 304 will pass through second transmissive linear polariser 304 and onto detector 305 as shown by diagram 334. Those skilled in the art will realise that approximately half of the forward emitted light, 317, will be absorbed by the polariser 304. The light, 319, will comprise forward emitted fluorescent light and light from the light source 301 that has not been absorbed by the polarising elements 302 and 306 and the sample, 303. The intensity of any remaining light from the light source, 301, that forms part of the light 319 will be greatly reduced through absorption by the linear polariser, 304.

Additionally, as shown in FIG. 3B, a back-emitted portion 321 of fluorescent light 317 is reflected off reflective polariser 306 and passes back towards detector 305. However only the component of the back-emitted radiation having a polarisation direction orthogonal to reflective polariser 306 will be reflected. This reflected light will pass through polariser 304 and onto detector 305. Thus, reflective linear polariser 306 acts to collect a back-emitted portion of fluorescent light which would otherwise have been lost hence increasing the sensitivity of the device.

In a modification not shown, the first linear polariser 302 is replaced by a circular polariser having its linear polariser adjacent to the reflective polariser, 306.

Figure 4A:
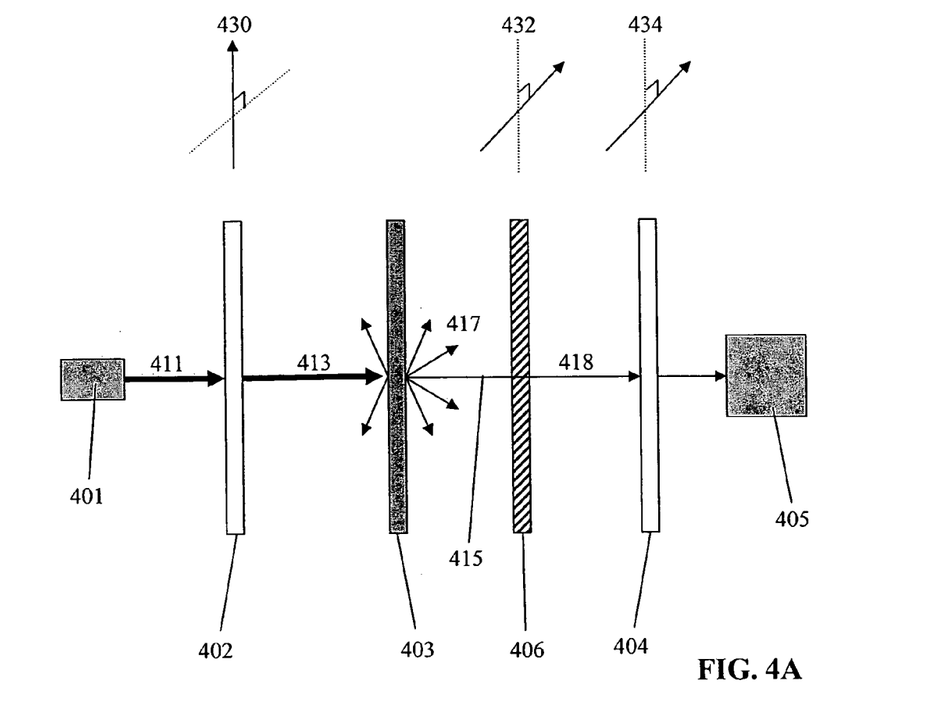
FIGS. 4A and 4B are schematics of a second embodiment of the present invention.
Figure 4B:
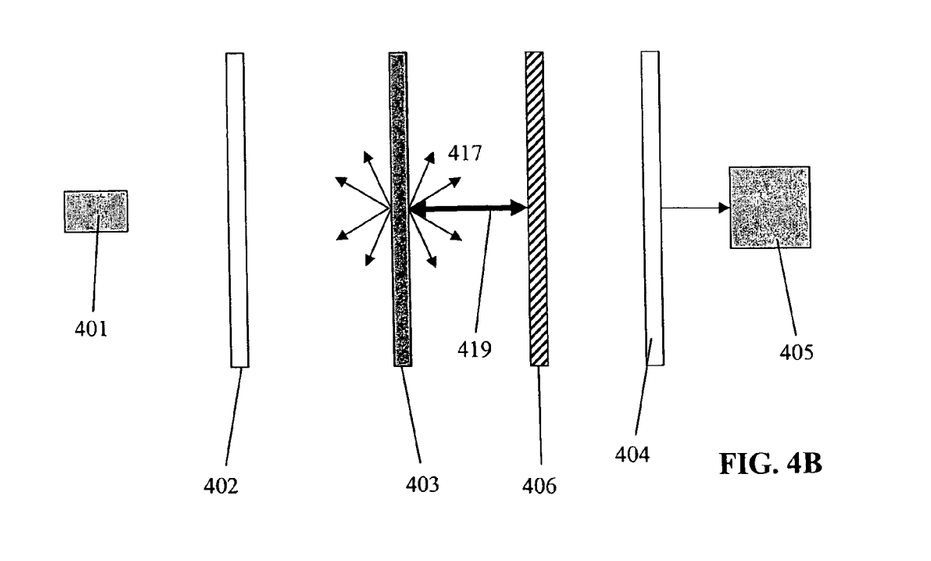

A second embodiment is shown in FIG. 4. Referring to FIG. 4 there is shown in series: a light source 401; a first linear transmissive polariser 402; a sample 403; a reflective linear polariser 406; a second linear transmissive polariser 404; and a light detector 405.

The polarisation directions of the reflective linear polariser 406 and the second linear transmissive polariser 404 are orthogonal to that of first linear transmissive polariser 402.

The properties of the reflective linear polariser 406 are that it reflects light polarised by the linear polariser 402 and transmits orthogonally polarised light.

Referring to FIG. 4A, therefore, light 411 is emitted from light source 401 and linearly polarised by the first linear transmissive polariser 402 as shown by diagram 430. Polarised light 413 is incident upon sample 403. If sample 403 contains a fluorophor, it will absorb light 413 and emit unpolarised fluorescent light 417. The unpolarised fluorescent light, 417, any remaining unabsorbed light from the light source, 401, will combine to produce light 415. A portion 418 of fluorescent light 417 is polarised by the reflective linear polariser 406 as shown by diagram 432 and passes through the second linear transmissive polariser 404 having the same polarisation direction, as shown by diagram 434. Very little of the florescent light 415 is lost due to the inclusion of 406 as the second linear transmissive polariser 404 would have eliminated light of the other polarisation anyway.

Since the sample 403 is partially transmissive, a portion of incident light passes through the sample 403 rather than being absorbed by it. As shown in FIG. 4B, the reflective linear polariser 406 reflects this transmitted incident light 419 from the light source 401 back onto sample 403 since reflective linear polariser 406 is orthogonal to polariser 402 in the transmission mode as shown in diagrams 430 and 432. Therefore more incident light is absorbed by the sample and the intensity of the fluorescent light 417 is substantially increased.

The intensity of any remaining light from the light source, 401, that forms part of the light 415 will be greatly reduced through reflection at the reflective polariser, 406, and absorption by the linear polariser, 304.

In a modification not shown the first linear transmissive polariser 402 is replaced by a circular polariser with its linear polariser adjacent to the sample 403.

Figure 5A:
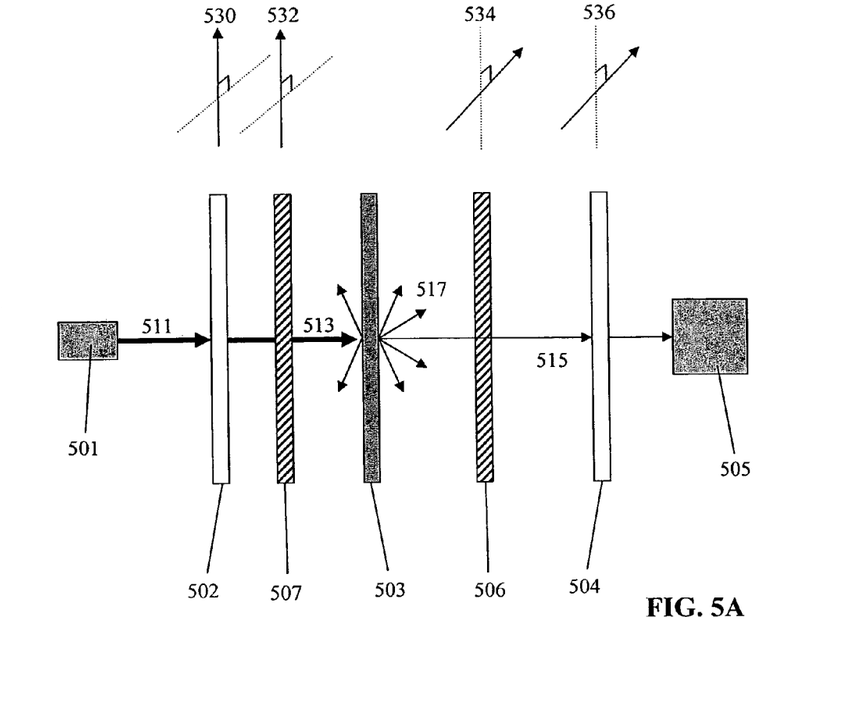
FIGS. 5A and 5B are schematics of a third embodiment of the present invention.
Figure 5B:
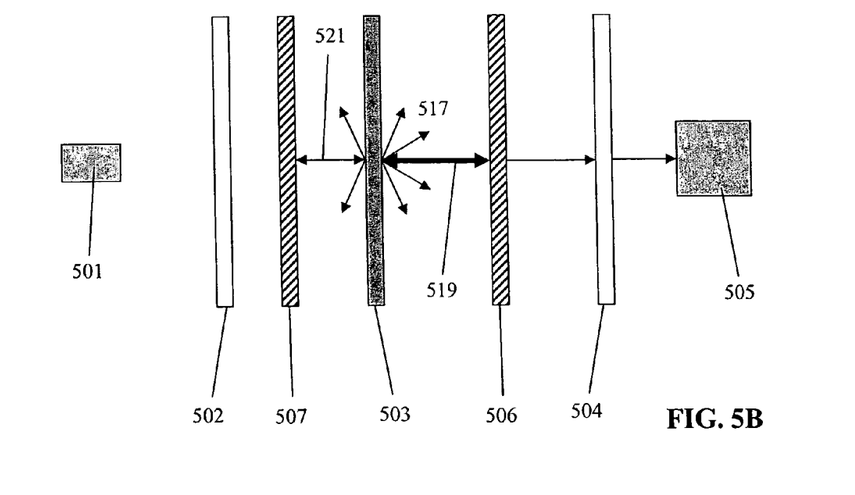

A third embodiment of the present invention is shown in FIG. 5 corresponding to a combination of the first two embodiments. Referring to FIG. 5A, there is shown in series: a light source 501; a first linear transmissive polariser 502; a first reflective linear polariser 507; a sample 503; a second reflective linear polariser 506; a second linear transmissive polariser 504; and a light detector 505.

In this third embodiment, the polarisation directions of the first linear transmissive polariser 502 and the first reflective linear polariser 507 in their transmission modes are orthogonal to the polarisation directions of the second reflective linear polariser 506 and the second transmissive linear polariser 504 in their transmission modes, as shown by diagrams 530, 532, 534 and 536

Referring to FIGS. 5A and 5B, light 511 from the light source 501 is linearly polarised by first linear transmissive polariser 502, passes through first reflective polariser 507 and onto sample 503. As described in more detail with respect to the second embodiment, some transmitted incident light 519 passes through the sample 503, reflects off the second reflective linear polariser 506 and makes a second pass of the sample 503. Therefore, illuminating the sample 503 and increasing the level of fluorescence.

Furthermore, as described in more detail with respect to the first embodiment, a portion of the back-emitted fluorescent light 521 will be reflected by the first reflective linear polariser 507, pass back through the sample 503, be polarised by the second reflective linear polariser 506, passes through the second linear transmissive polariser 504 and reach the light detector 505. Approximately half of the front-emitted fluorescent light 515 will also be polarised by the second reflective linear polariser 506, pass through the second linear transmissive polariser 504 and reach the detector 505.

Figure 6:
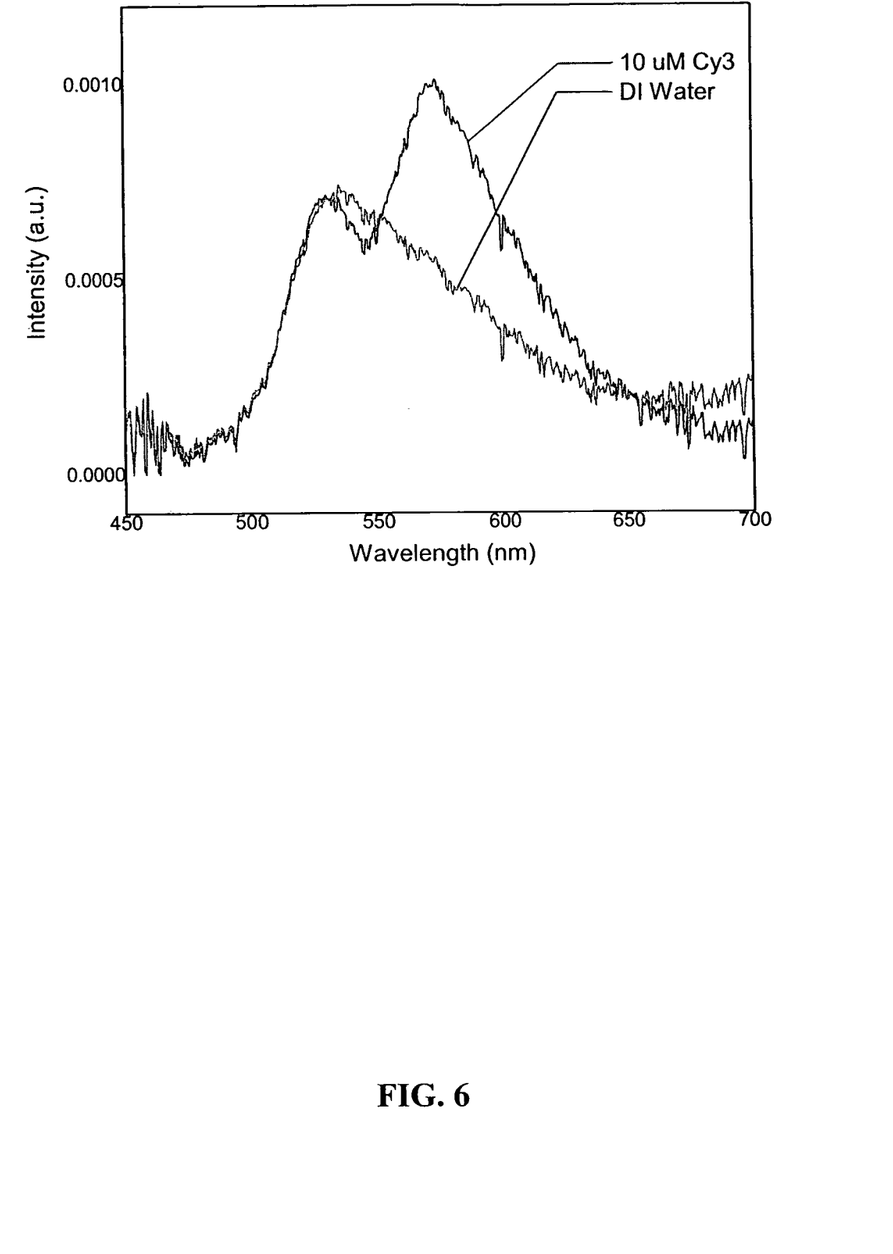
FIG. 6 shows a result obtained using the third embodiment.

An example result obtained using the third embodiment is shown in FIG. 6. Referring to FIG. 6, there is shown the detected signal from an example fluorophor, Cy3 (10 micromolar concentration) available from GE Healthcare, having a first peak at approximately 530 nm, corresponding to light from the source transmitted through the sample, and a second peak at approximately 575 nm corresponding to the emitted fluorescence. For comparison, the signal detected with water as the target is also shown. The absence of the second peak with water confirms no fluorescent light was emitted.

Figure 7:
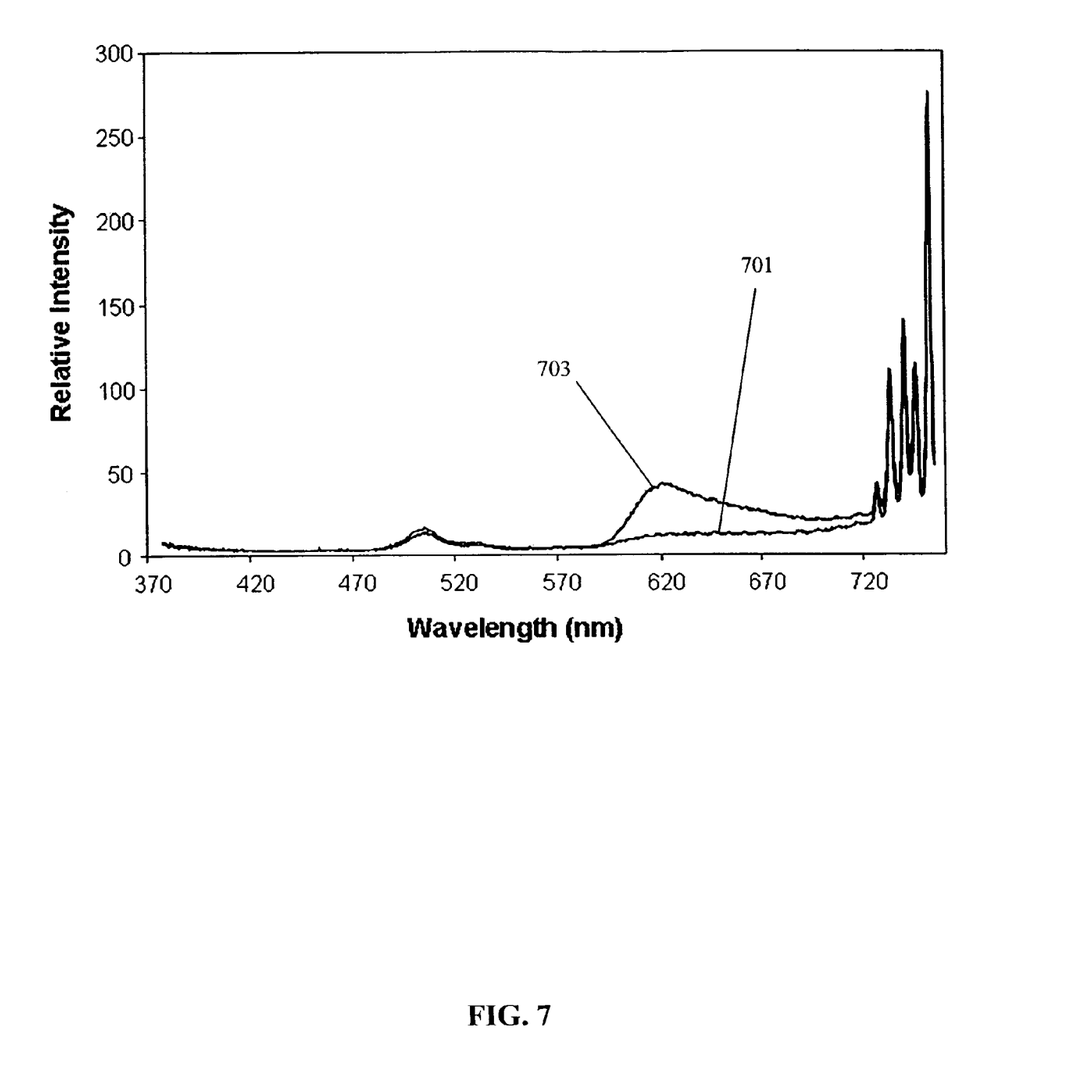
FIG. 7 shows a second result obtained using the third embodiment combined with short pass and long pass optical filters.

A further example result using the third embodiment is shown in FIG. 7. The results shown in FIG. 7 were obtained using an inorganic green LED (530 nm) light source available from TOYODA GOSEI as part number E1S02-4G0A7, the Lee Filters Dark Green (No. 124) and Jas Green (No. 738) for short pass filter (SPF) placed between the light source and the first linear polariser, the Lee Filters Fire (No. 019) and Magenta (No. 113) for long pass filter (LPF) placed between the second linear polariser and the photodetector. The sample placed between the two reflective polarisers was Albumin with a concentration of 40 mg/l with AB-580 (shown as Plot 703 in FIG. 7). For reference, the trace obtained with a sample of air is shown (Plot 701 of FIG. 7). The photodetector was an organic photodetector. It was found that this detector is advantageous in that it effectively does not detect light beyond 650 nm. This is advantageous because it has been found that in the present system there is a significant intensity of extraneous light beyond 650 nm, which is illustrated in FIG. 7.

In a modification not shown, the addition of a longpass filter between the second transmissive polariser and the light detector leads to a further reduction in the intensity of residual light from the light source and in addition to that provided by the use of the first and second crossed linear polarisers. This is particularly advantageous if the Stokes shift between the absorption maximum and the emission maximum of the fluorphor is at least 50 nm.

The skilled reader will understand that any light source capable of inducing the required emission from the sample is suitable for any embodiment of the present invention, for example, the lime green polymer OLED, part number Q65110A5706 supplied by Pictiva, a subsidiary of Osram Malaysia The light source may be an organic light emitting diode based on polymers, small organic molecules or dendrimer molecules. The light source could also be an inorganic light emitting diode.

The skilled reader will also understand that any transmissive polariser capable of polarising at the wavelength of the light source and the wavelength of the fluorescent light is suitable, for example, polarising film, part number NPF-G1220, supplied by Nitto Denko Corporation, Japan. In addition, any reflective linear polariser suitable for the light source and fluorescence wavelength is suitable; for example, a Dual Brightness Enhancement Film available from 3M or a cholesteric liquid crystal polarising device as known from U.S. Pat. No. 6,016,177A, the contents of which are incorporated herein by reference, for example.

Any light detector capable of detecting light at the wavelength of the fluorescent light may be suitable. For example, the detector can be an organic detector comprising an organic photoactive material, such as a semi-conducting polymer. A detector comprising a blend of two organic semi-conducting polymers to form the active layer of the photodetector, for example, as described in U.S. Pat. No. 5,670,791, can be used. A particularly useful detector comprises a layer of regioregular poly(3-hexylthiophene), commonly known as P3HT, and 1-(3-methoxycabonylpropyl)-1-phenyl[6,6]C61, commonly known as PCBM, arranged between a transparent electrode, such as one formed from ITO and PEDOT:PSS, and a second electrode, for example, comprising a layer of aluminium. In a specific embodiment, the P3HT/PCBM layer is a 160 nm layer and the second electrode comprises a 100 nm layer of aluminium. Of course, reference to "optical" and "light" extend to radiation in any part of the spectrum. The skilled reader will understand the invention is not limited to a semi-conducting polymer detector but instead could be any detector capable of detecting radiation at the emitted wavelength such as a suitable silicon photodiode or solar cell.

To those skilled in the art it will be apparent that any appropriate polariser, linear or otherwise, can be employed for example, the linear polariser could be a combination of two or more linear polarisers, to exclude more of the light that has leaked through the first linear polariser, or a combination of a circular polariser with a linear polariser in order to increase the degree of polarisation of the light from the light source. The linear polarisers can be provided in any appropriate order that allows filtering out of the light from the light source.

The skilled person will also realise that the claimed invention is equally applicable to detecting phosphorescence in samples. In fact, as the skilled reader will be aware, the claimed invention is applicable to detecting any light emitted from a sample illuminated by polarised light.

Embodiments of the present invention provide an improved optical detection system wherein more fluorescent light is collected owing to the use of reflective and transmissive linear polarisers. This is achieved by capturing some of the back-reflected light and causing the stimulating light to make two passes of the sample. Embodiments enable the detection system to use an in-line geometry and a small light source and detector. Embodiments have the advantage of being lower cost than systems using highly selective optical filters as described in the prior art.

The invention claimed is:

1. A detector apparatus for detecting radiation emitted by a target comprising:
   a first transmissive polariser for polarising, with a first polarisation, a first radiation incident on the target on a first pass;
   a second transmissive polariser arranged to substantially extinguish radiation with the first polarisation;
   a target region therebetween;
   a detector arranged to receive radiation transmitted by the second transmissive polariser;
   a first reflective polariser arranged between the first and second transmissive polarisers to redirect first radiation, transmitted through the target region on the first pass, back towards the target region for a second pass and such that light with the first polarisation is sent towards the target region and light with a second polarisation is sent towards the detector.

2. A detector apparatus as claimed in claim 1 wherein the polarisation direction of the first transmissive polariser is orthogonal to that of the second transmissive polariser.

3. A detector apparatus as claimed in claim 1 wherein the first reflective polariser is between the target region and the second transmissive polariser and is polarised, in transmission, parallel to the second transmissive polariser.

4. A detector apparatus for detecting radiation emitted by a target comprising:
   a first transmissive polariser for polarising, with a first polarisation, radiation incident on the target;

a second transmissive polariser arranged to substantially extinguish radiation with the first polarisation;

a target region therebetween;

a detector arranged to receive radiation transmitted by the second transmissive polariser;

a first reflective polariser arranged between the first and second transmissive polarisers to redirect light emitted or transmitted by the target region towards the target region and such that light with the first polarisation is sent towards the target region and light with a second polarisation is sent towards the detector;

a second reflective polariser arranged between the first and second transmissive polarisers such that light with the first polarisation is sent towards the target region and light with a second polarisation is sent towards the detector, wherein the first reflective polariser is between the first transmissive polariser and the target region and is polarised, in transmission, parallel to the first transmissive polarizer.

5. A detector apparatus as claimed in claim 4 wherein the second reflective polariser is arranged between the target region and the second transmissive polariser and polarised, in transmission, parallel to the second transmissive polariser.

6. A detector apparatus as claimed in claim 1 wherein the first transmissive polariser, second transmissive polariser, detector, first reflective polariser and second reflective polariser are arranged substantially on a common optical axis.

7. A detector apparatus as claimed in claim 1 wherein the first transmissive polariser is a circular polariser.

8. A detector apparatus as claimed in claim 1 further comprising a light source.

9. A detector apparatus as claimed in claim 8 wherein the light source is an organic light emitting diode based on small organic molecules or dendrimer molecules.

10. A detector apparatus as claimed in claim 8 wherein the light source is an inorganic light emitting diode.

11. A detector apparatus as claimed in claim 8 wherein the light source is a polymer light emitting diode.

12. A detector apparatus as claimed in claim 1 wherein the detector comprises an organic photovoltaic device or photodiode.

13. A detector apparatus as claimed in claim 1 wherein the detector comprises a silicon photodiode or a solar cell.

14. A detector apparatus as claimed in claim 1 wherein the first radiation is optical radiation.

15. A detector apparatus as claimed in claim 1 wherein the first and second transmissive polarisers are linear polarisers.

16. A detector apparatus as claimed in claim 1 wherein the first transmissive polariser is a circular polariser.

17. A detector apparatus as claimed in claim 1 further comprising a target support for supporting the target.

18. A detector apparatus as claimed in claim 1 further comprising a target.

19. A detector apparatus as claimed in claim 1 further comprising a longpass filter between the second transmissive polariser and the detector.

20. A method of detecting radiation emitted by a target comprising directing radiation onto the target;

detecting radiation emitted by the target using a detector apparatus comprising a first transmissive polariser for polarising, with a first polarisation, a first radiation incident on the target on a first pass; a second transmissive polariser arranged to substantially extinguish radiation with the first polarisation; a target region therebetween; a detector arranged to receive radiation transmitted by the second transmissive polariser; a first reflective polariser arranged between the first and second transmissive polarisers to redirect first radiation, transmitted through the target region towards the target region for a second pass and such that light with the first polarisation is sent towards the target region and light with a second polarisation is sent towards the detector.

21. A method of detecting radiation as claimed in claim 20 wherein the incident light is substantially at a first wavelength and the emitted light is substantially at a second wavelength.

22. A method of detecting radiation as claimed in claim 20 wherein the first wavelength and the second wavelength differ by less than 50 nm.

23. A method of detecting radiation as claimed in claim 20 wherein a difference between the first wavelength and the second wavelength represents a Stokes shift.

24. A method of detecting radiation as claimed in claim 20 wherein the emitted light results from fluorescence.

25. A method of detecting radiation as claimed in claim 20 wherein the emitted light results from phosphorescence.

26. A method of detecting radiation as claimed in claim 20 wherein the incident light is polarised and the emitted light is unpolarised.

27. A method of detecting radiation as claimed in claim 20 wherein the first wavelength and the second wavelength differ by 30-50 nm.

28. A detector apparatus for detecting radiation emitted by a target comprising:

a first transmissive polariser for polarising, with a first polarisation, radiation incident on the target;

a second transmissive polariser arranged to substantially extinguish radiation with the first polarisation;

a target region therebetween;

a detector arranged to receive radiation transmitted by the second transmissive polariser;

a first reflective polariser arranged between the first and second transmissive polarisers to redirect light emitted by the target region away from the detector, back through the target region and towards the detector, and such that light with the first polarisation is sent towards the target region and light with a second polarisation is sent towards the detector.

* * * * *